United States Patent [19]

Babb et al.

[11] Patent Number: 4,751,178
[45] Date of Patent: Jun. 14, 1988

[54] SUBSTRATES, COMPOSITIONS, ELEMENTS AND METHODS FOR THE DETERMINATION OF GAMMA-GLUTAMYLTRANSFERASE

[75] Inventors: Bruce E. Babb, Rochester; Roy E. Snoke, Webster, both of N.Y.

[73] Assignee: Eastman Kodak Company, Rochester, N.Y.

[21] Appl. No.: 780,508

[22] Filed: Sep. 26, 1985

[51] Int. Cl.$^4$ .............................................. C12Q 1/48
[52] U.S. Cl. ....................................... 435/15; 435/16; 435/24; 435/805; 546/141; 546/142; 546/143; 546/153; 546/155; 546/159
[58] Field of Search ................. 435/15, 16, 24, 805; 546/141, 142, 143, 153, 159, 155

[56] References Cited

U.S. PATENT DOCUMENTS

| | | | |
|---|---|---|---|
| 3,703,441 | 11/1972 | Nakanishi et al. | 435/24 |
| 3,979,447 | 9/1976 | Bernt et al. | 435/15 |
| 4,087,331 | 5/1978 | Bucolo | 435/15 |
| 4,167,449 | 9/1979 | Gargiulo | 435/16 |
| 4,177,109 | 12/1979 | Tohyama et al. | 435/24 |
| 4,560,650 | 12/1985 | Bauer, III | 435/15 |
| 4,567,138 | 1/1986 | Beck | 435/15 |
| 4,603,107 | 7/1986 | Deneke | 435/24 |

FOREIGN PATENT DOCUMENTS 6097260 8/1981 Japan ..................... 435/15

Primary Examiner—Robert J. Warden
Assistant Examiner—Robert Benson
Attorney, Agent, or Firm—J. Jeffrey Hawley

[57] ABSTRACT

New substrates for γ-glutamyltransferase (γ-GT) are disclosed. These substrates are useful in the colorimetric determination of γ-GT since the cleavage of the γ-glutamyl group produces a detectable species—an aminostyrylquinolinium dye. The substrates have the formula:

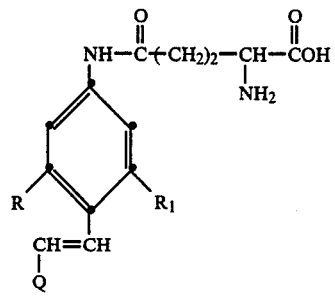

wherein:
R and $R_1$ are independently selected from hydrogen, alkyl and alkoxy and
Q is

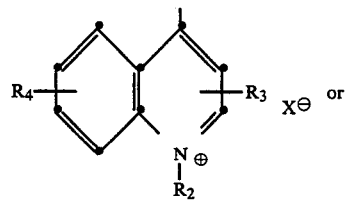 or

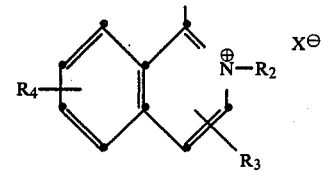

wherein:
$R_2$ is alkyl having from 1 to 4 carbon atoms;
$R_3$ and $R_4$ are independently selected from hydrogen, alkyl, alkoxy, nitro, cyano and halogen; and
$X^{\ominus}$ is an anion.

10 Claims, No Drawings

SUBSTRATES, COMPOSITIONS, ELEMENTS AND METHODS FOR THE DETERMINATION OF GAMMA-GLUTAMYLTRANSFERASE

FIELD OF THE INVENTION

The present invention relates to new substrates, compositions, elements and methods for the colorimetric determination of the enzyme γ-glutamyltransferase.

DESCRIPTION RELATIVE TO THE PRIOR ART

The activity of gamma-glutamyltransferase (hereinafter γ-GT) is one of the most routinely measured serum enzyme activities in clinical evaluations. The measurement of γ-GT activity in blood serum is a useful testing method for detecting diseases of the liver. This enzyme catalyses the transfer of a gamma-glutamyl group.

In general, there are two basic methods for the determination of γ-GT. The first method is the direct method and involves the direct release of a detectable species by the γ-GT enzyme. The most common method of this type involves the use of the substrate γ-glutamyl-p-nitroanilide. A reagent composition comprising this substrate is mixed with the serum sample suspected of containing γ-GT. If there is γ-GT in the sample, the glutamyl group is cleaved from the substrate releasing para-nitroaniline which can be detected. Several problems with this substrate have been noted. For example, it is less soluble than desired and therefore in assays using this substrate, the reaction mixture is usually substrate limited. Obviously, where it is desired to measure the amount of enzyme, it is important to have an excess of the substrate. Thus, there have been several proposals to overcome this problem. For example, surfactants have been used or, the substrate has been modified by the addition of solubilizing groups so as to make the substrate more soluble in the reaction mixture. Representative patents disclosing these types of modifications are U.S. Pat. Nos. 3,703,441 and 3,979,447.

A second problem which has been noticed with this direct method is that the detectable species which is released has a maximum absorption in the 400 nanometer range. Unfortunately, many blood components such as hemoglobin and bilirubin also absorb in this range and it is therefore difficult to detect the para-nitroaniline in the presence of these other blood components. As a result, a blank must be run with each sample. This adds complexity, inaccuracy and cost to the measurement of the γ-GT.

Largely as a result of this second problem, the indirect method has been developed. In this method, the γ-GT catalyzes the release of the glutamyl group from a substrate. The remainder of this substrate (minus the glutamyl group) is capable of reacting with another reagent to produce a dye which absorbs away from the 400 nanometer region of the spectrum. Other reagents which have been suggested include oxidizing agents and couplers. However, the addition of these other reagents adds additional complexity and cost as well as providing an opportunity for additional interfering reactions to occur. Methods of this latter type are exemplified by U.S. Pat. No. 4,177,109 wherein a para-phenylenediamine is released when the γ-GT reacts on the substrate and the para-phenylenediamine is then reacted with a diazo coupling compound, an aldehyde derivative or similar reagents to form the chromogen that is detected.

STATEMENT OF THE PROBLEM

From the foregoing, it is readily apparent that there is a continuing need for substrates which can be used in γ-GT analysis. The substrate and method should overcome the problems of both the direct method and the method requiring additional reagents. The γ-GT substrate which is used should have a high solubility so that the reaction for the measurement of γ-GT is not substrate limited and should produce a species which absorbs in a region different from the 400 nm region.

SUMMARY OF THE INVENTION

It has been found that certain γ-glutamido-substituted styrylquinolinium salts are excellent substrates for the determination of γ-GT. Useful salts have the structural formula:

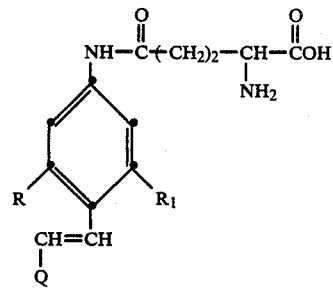

wherein:
R and R₁ are independently selected from hydrogen, alkyl and alkoxy and
Q is

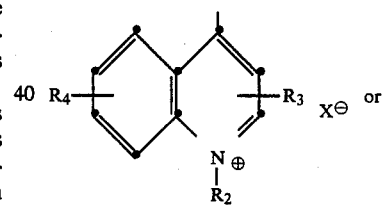

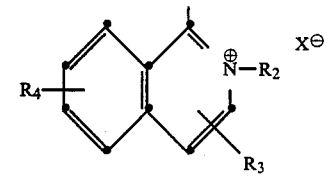

wherein:
R$_2$ is alkyl having from 1 to 4 carbon atoms;
R$_3$ and R$_4$ are independently selected from hydrogen, alkyl, alkoxy, nitro, cyano and halogen; and
X$^\ominus$ is an anion.

According to the present invention, γ-glutamyltransferase can be determined by the steps of contacting a sample suspected of containing the γ-GT with a reagent composition including the substrate described above and an acceptor for γ-glutamyl and measuring the rate at which the aminostyrylquinolinium dye is produced.

In another aspect, the invention relates to an analytical element comprising a support having thereon a zone or zones containing the described reagent composition.

The action of the γ-GT on the described substrate results in the transfer of the γ-glutamyl group to the γ-glutamyl acceptor with the simultaneous production of an aminostyrylquinolinium dye. The removal of the γ-glutamyl group leaves behind an amine group on the dye. The substrate containing the γ-glutamyl group and the resulting aminostyrylquinolinium dye have greatly different absorption characteristics so that they can be easily differentiated. Further, the aminostyrylquinolinium dye has a maximum absorption at 448 nanometers and a significant amount of absorption as far out as 510 nanometers. Thus, the formation of the dye can be monitored above 500 nanometers. This wavelength is away from the absorptions of some interfering substances in the blood. This absorption shift is achieved without the need for auxiliary reagents to react with the product of substrate cleavage. Thus, the reagent composition for the determination of γ-glutamyltransferase can include simply a γ-glutamido-substituted styrylquinolinium salt and a γ-glutamyl acceptor.

DETAILED DESCRIPTION OF THE INVENTION

The γ-GT substrates of the present invention have the structural formula:

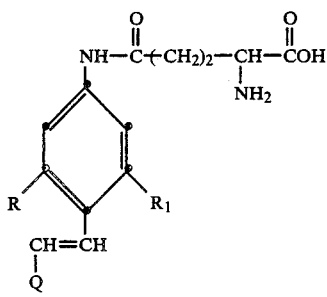

wherein:

R and $R_1$ are independently selected from hydrogen, alkyl (including substituted alkyl), preferably having from 1 to 10 carbon atoms such as methyl, ethyl, decyl and chloromethyl, alkoxy (including substituted alkoxy), preferably having 1 to 10 carbon atoms such as methoxy, ethoxy and decyloxy;

Q is

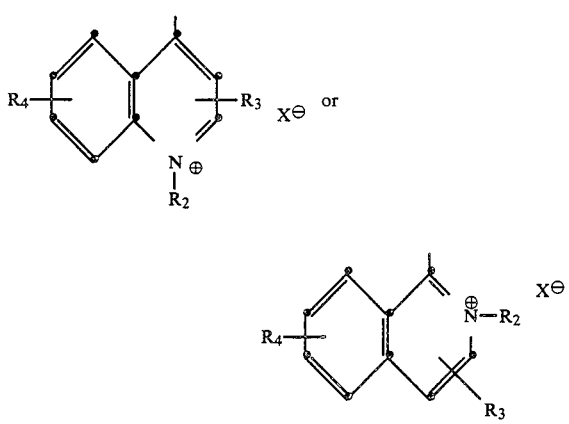

wherein:

$R_2$ is alkyl (including substituted alkyl) having from 1 to 4 carbon atoms such as methyl, isopropyl and chlorobutyl;

$R_3$ and $R_4$ are independently selected from hydrogen, alkyl, alkoxy (including substituted alkyl and alkoxy) as mentioned for R and $R_1$ and nitro, cyano, amino, sulfonamido and halogen such as chloro and bromo; and $X^\ominus$ is an anion.

The preferred compound according to the present invention is N-methyl-4-(4'-(γ-glutamido)styryl)-quinolinium tetrafluoroborate. The preparation of this compound is illustrative of the preparation of other compounds within the scope of the invention and is described in detail below.

In the formula above, $X^\ominus$ an anion. The nature of the anion does not effect the ability of the compound to be a substrace for γ-GT and any anion can be used, for example, halo including fluoro, chloro, bromo and iodo; aryl sulfonates such as p-toluenesulfonate; perchlorate and the like. Halogenated anions such as tetrafluoroborate, hexafluorophosphate, chlorozincate and hexafluorotitinate are slightly less soluble than, for example, the highly soluble chloro compounds and are therefore easier to isolate.

In the determination of γ-GT a γ-glutamyl acceptor is included. The preferred acceptor is glycylglycine since it also functions as a buffer. Other acceptors for the glutamyl radical from the substrates of the invention include aspartic acid, methionine and L-phenylalanine.

In addition to the substrate of the invention and a glutamyl acceptor, reagents for the determination of γ-GT optionally include a buffer. The reaction mixture should be buffered to a pH of between 6 and 9, preferably between 8.0 and 8.5. Preferred buffers to provide this pH include glycylglycine which performs the dual function of being the acceptor and the buffer, tris(hydroxymethyl)aminomethane, also known as TRIS or its hydrochloride salt, N-2-hydroxypiperazine-N'-2-ethane sulfonic acid (HEPES), 1,4-piperazinediethane sulfonic acid (PIPES), as well as other buffers known in the art.

The reagent composition including the substrate of the present invention contains the reactants in conventional quantities. For example, the substrate of the invention can be present in the final reaction mixture in an amount from about 0.1 to about 5 mM, preferably 0.3 to 1.5 mM; the glutamyl acceptor in an amount from about 10 to about 500 mM, preferably 50 to 150 mM; and the buffer in an amount from about 50 to about 250 mM, preferably 75 to 150 mM.

The reagent composition is prepared in a variety of forms. For example, the reagent optionally is prepared as a lyophilyzed powder or tablets which are reconstituted with water to produce a reagent solution. Techniques for making such forms of reagent compositions and materials such as fillers, binders and the like are well known in the art.

The γ-GT substrates of the present invention are useful in conventional solution assays and in dry analytical elements. A solution assay is carried out by adding a sample suspected of containing the γ-GT to a reagent composition containing the described γ-GT substrate and a γ-glutamyl acceptor. The resulting solution is kept for a time at a set temperature, typically up to 30 minutes at a temperature up to 40° C. The presence of γ-GT in the resulting reaction mixture is indicated by a change in color of the mixture which can be detected using conventional spectrophotometric techniques using a wavelength above 500 nanometers. The rate of dye formation is proportional to γ-GT enzyme concentration. Where a dry analytical element is desired, the reagent composition is coated on a suitable support and the resulting layer is dried. Contact of the element with a sample dissolves the reagent and again, in the presence of γ-GT, the resultant color change can be measured.

In its simplest form, dry analytical elements of the present invention comprise a carrier matrix impregnated with the described reagent composition. Useful carrier matrixes are insoluble and maintain their structural integrity when exposed to water or physiological fluids such as serum or urine. Useful carrier matrixes include paper, cellulose, wood, glass fiber, woven and nonwoven fabrics. A useful dry analytical element is made by imbibing a solution containing the reagent composition in the matrix and drying.

The element can also comprise a layered or zoned structure having reagents in the layers or zones. One type of structure includes a spreading layer which can be an isotropically porous polymer or a fabric. Useful materials and elements which can use the described reagent composition are described, for example, in U.S. Pat. Nos. 3,092,465, 3,418,099, 3,418,083, 2,893,843, 2,893,844, 2,912,309, 3,008,879, 3,802,842, 3,798,064, 3,298,739, 3,915,647, 3,917,453, 3,993,594, 3,936,357, 4,270,920, 4,248,829, 4,255,384, 4,256,693, and U.K. Pat. No. 2,052,057.

In preferred dry analytical elements the element comprises a support having thereon a non-fibrous isotropically porous spreading layer. The spreading layer has therein the described reagent composition. It is desirable to include the reagent composition in such a porous spreading layer, since γ-GT is a relatively large protein and the porous layer provides for better contact between the γ-GT and the reagent composition. Alternatively some of the reagents of the reagent composition can be in the spreading layer while other reagents can be in other layers such as layers commonly referred to as reagent layers. All reagents can be in these other layers.

Useful isotropically porous spreading layers are disclosed in U.S. Pat. No. 3,992,158. In one embodiment, particulate materials are used to form the layers and isotropic porosity is created by interconnected spaces between the particles. Alternatively, such layers are prepared using isotropically porous polymers, for example, "blush" polymers.

A preferred isotropically porous spreading layer contains particulate materials such as titanium dioxide. Microcrystalline cellulose, which is commercially available from FMC Corporation under the name Avicel ®, is another example of a material which is preferred for use in the present invention. A particularly preferred material is barium sulfate.

Another useful porous spreading layer is the bead spreading layer described in U.S. Pat. No. 4,258,001. The bead spreading layers of this patent contain polymer particles held together by a small amount of adhesive located between adjacent particles where the particles are in closest proximity.

The following preparation of N-methyl-4-(4'-(γ-glutamido)styryl)quinolinium fluoroborate is illustrative of the preparation of the compounds of the invention. The intermediates and final products were characterized by infrared spectroscopy and nuclear magnetic resonance analysis.

EXAMPLE 1

The Preparation of N-Methyl-4-(4'(γ-glutamidostyryl))quinolinium fluoroborate

Step 1: The Preparation of Intermediate A

N-Methyllepidinium iodide (285 g, 1 mol ) and p-acetamido benzaldehyde (163 g, 1 mol) were dissolved in methanol (1200 mL) by heating the mixture to a boil. Piperidine (10 mL) was added with stirring and the solution was heated in a 55° C. water bath for 3 hours. The mixture was cooled in an ice bath, the rust-colored solid was filtered off, washed with a small volume of cold methanol, then with ether and finally dried in a steam cabinet to yield 335 g (78%) of Intermediate A.

Step 2: The Preparation of Intermediate B

N-Methyl-4(4'-acetamidostyryl)quinolinium iodide (Intermediate A, 200 g, 0.47 mol) was heated under reflux for 1 hour with a solution of 200 mL 48% HBr in 1 L glacial acetic acid. The mixture was cooled and the product was collected by filtration, washed with a small amount of ether, then dried in a steam cabinet. The yield was 166 g of the amine hydrobromide. The free amine was obtained by the following procedure: the hydrobromide salt was dissolved in 2 L boiling water containing a few mL of 48% HBr and then 100 mL pyridine was added to the hot solution. The mixture was cooled in an ice bath, and the dye was filtered off as magenta plates which were dried in a steam cabinet overnight. The yield was 131 g (83%) of Intermediate B.

Step 3: The Preparation of Intermediate C

Trifluoroacetic anhydride (500 g, 2.38 mol) were placed in a 2 L flask in an ice bath. L(+)-glutamic acid (166 g, 1.13 mol) was added all at once, to the cold stirred anhydride. After a few minutes, the slurry set up almost solid, then became hot as the solid dissolved. As the solid went into solution, the reaction almost came to a boil. The solution was cooled to room temperature. Two such batches were combined and the trifluoroacetic acid was removed by vacuum evaporation. One liter of dry ether was added to the residue. The syrup first dissolved, then began crystallizing out as lustrous white plates. The mixture was chilled overnight. The product was filtered off, washed with dry ether, and dried in a vacuum oven at room temperature. The yield was 320 g (63%) of Intermediate C.

Step 4: The Preparation of Intermediate D

A mixture of 70 g (0.21 mol) N-methyl 4(4'-aminostyryl)quinolinium bromide (Intermediate B), 60 g (0.27 mol), trifluoroacetylglutamic anhydride (Intermediate C) and 350 mL dry N,N-dimethylformamide (DMF) was heated on a steam bath with stirring until no more starting material was observed by thin layer chromatography (TLC). Almost all of the DMF was removed by vacuum evaporation and the residue started to solidify.

The residue was stirred with alcohol for an hour and then chilled overnight. The orange solid was filtered off, washed with alcohol, then dried in a steam cabinet. The yield was 82 g (71%) of Intermediate D. TLC (silica, 9:1 acetic acid:$H_2O$), one spot, $R_f=0.75$.

Step 5: The Preparation of N-Methyl-4-(4'-(γ-glutamidostyryl))quinolinium fluoroborate Intermediate D (82 g, 0.14 mol) was added with stirring to a solution of 25 g of 50% NaOH diluted to 800 mL with ice and ice water. The cold solution was stirred for about an hour, then made acidic with glacial acetic acid. The mixture was warmed slightly to redissolve some solid which had separated. A filtered solution of sodium fluoroborate (32 g, 0.29 mol) in 100 mL H₂O was added with stirring. The mixture was chilled in an ice bath, then filtered to remove most of the water. The remaining sticky solid was stirred overnight with 1 L of alcohol. The product was filtered off and washed with acetone, then ether and dried in air at room temperature. The yield was 68 g of free amine. The tetrafluoroborate salt was purified by the following procedure:

One hundred grams of the product from the previous step was dissolved in 1 L boiling water containing sodium fluoroborate (25 g, 0.23 mol) and 50 mL glacial acetic acid. Decolorizing carbon (10 g) was added, and the solution was filtered while hot. It was allowed to cool to room temperature, then chilled overnight. The solid was filtered off and washed with ice water, then with alcohol, and finally with ether. The product was dried in a steam oven at about 50° C. The yield was 97 g of N-methyl-4-(4'-(γ-glutamidostyryl))quinolinium fluoroborate (γ-GASQ). TLC silica, 1:9 H₂O: CH₃COOH), one spot, R$_f$=0.4.

EXAMPLE 2

Spectra of the Preferred γ-GT Substrate and the Corresponding Dye

The substrate and the aminostyrylquinolinium dye (no γ-glutamyl group) were separately dissolved in 0.1 M TRIS buffer (pH 8.5), containing 0.075 M glycylglycine. Their spectra were recorded in a spectrophotometer. The quinolinium dye not only showed a substantial bathochromic shift of 50 nm over the substrate, but also a greatly increased maximum absorption.

EXAMPLE 3

Rate of Product Formation Versus Enzyme Levels

The reaction catalyzed by γ-GT when γ-GASQ is used as a substrate is as follows:

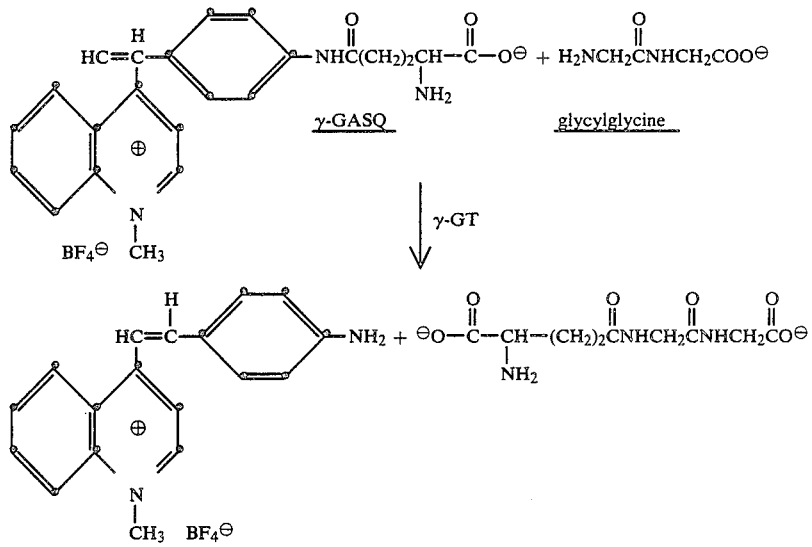

The rate of formation of the aminostyrylquinolinium dye was measured at different levels of γ-GT, which were prepared from a stock solution containing 44.5 units of enzyme per liter. γ-GT was added to a mixture of glycylglycine (0.075 M), γ-GASQ (0.5 mM) and TRIS-chloride buffer (0.1 M) at pH 8.5, 37° C. The change in absorbance was measured at 510 nm in a spectrophotometer. The rate of change in absorbance was plotted against the γ-GT activity. The straight line that resulted indicated that the rate of product formation was directly proportional to the amount of enzyme added.

EXAMPLE 4 pH-Activity Profile

γ-GT activity, using γ-GASQ as the substrate, was measured at pH values between 6–9. Glycylglycine was used both as an acceptor substrate and assay buffer. Various levels of γ-GT were added to glycylglycine (0.1 M) and γ-GASQ (1.5 mM). The reaction was monitored at 510 nm. Each pH value was determined by measuring the pH of each reaction mixture immediately following the reaction. γ-GT was most active at assay pH values 8.0 to 8.5 and had some activity at pH 6 and pH 9.

Example 5

Kinetic Study of γ-GT and Preferred Substrate

Initial velocity reaction rates and kinetic parameters for porcine kidney γ-GT were determined at 510 nm using a substrate of this invention (γ-GASQ) at a concentration range of 0.375 to 1.50 mM and glycylglycine at a concentration of 100 mM. Glycylglycine was used as a buffer (pH 8.4) and an acceptor. From the data obtained, a Lineweaver-Burk plot was constructed. The Michaelis-Menton constant (Km), calculated from this plot, had a value of 0.56 mM for the new substrate, indicating a significant enzyme-substrate affinity. The overall rate of reaction (Vmax) was calculated to be 0.5 γmole/minute/mL of enzyme. The enzyme activity with the new substrate was 0.36 μmole/minute/mL of enzyme. This data indicates that γ-GASQ is an effective substrate for γ-GT.

The invention has been described in detail with particular reference to preferred embodiments thereof, but it will be understood that variations and modifications can be effected within the spirit and scope of the invention.

What is claimed is:

1. A compound of the formula:

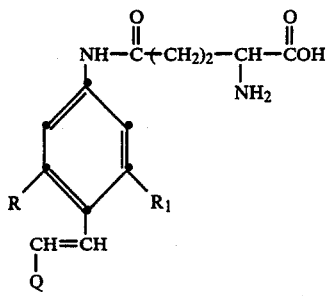

wherein:
R and $R_1$ are independently selected from hydrogen, alkyl and alkoxy and
Q is

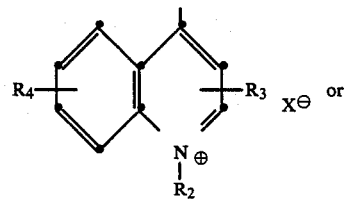

wherein:
$R_2$ is alkyl having from 1 to 4 carbon atoms;
$R_3$ and $R_4$ are independently selected from hydrogen, alkyl, alkoxy, nitro, cyano and halogen; and
$X^\ominus$ is an anion.

2. A compound according to claim 1 wherein:
Q is

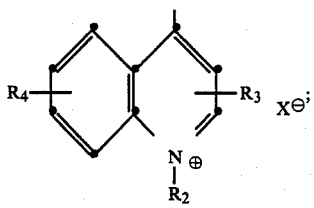

R, $R_1$, $R_3$ and $R_4$ are hydrogen;
$R_2$ is methyl, and
$X^\ominus$ is tetrafluoroborate.

3. A reagent composition comprising a γ-glutamyltransferase substrate having the formula:

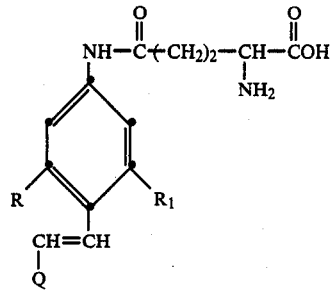

wherein:
R and $R_1$ are independently selected from hydrogen, alkyl and alkoxy and
Q is

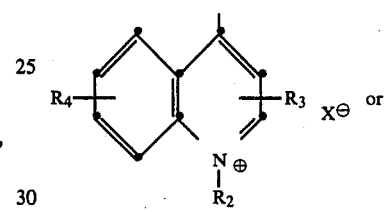

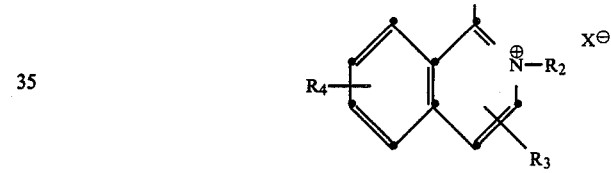

wherein:
$R_2$ is alkyl having from 1 to 4 carbon atoms;
$R_3$ and $R_4$ are independently selected from hydrogen, alkyl, alkoxy, nitro, cyano and halogen; and
$X^\ominus$ is an anion;
and an acceptor for γ-glutamyl.

4. The composition according to claim 3 wherein said acceptor is glycylglycine.

5. The composition according to claim 3 wherein:
Q is

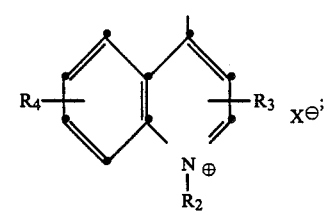

R, $R_1$, $R_3$ and $R_4$ are hydrogen;
$R_2$ is methyl; and
$X^\ominus$ is tetrafluoroborate.

6. The composition according to claim 3 further comprising a buffer.

7. An analytical element comprising a support having thereon a zone or zones containing a reagent composition for determining γ-glutamyltransferase wherein said reagent comprises a γ-glutamyltransferase substrate having the formula:

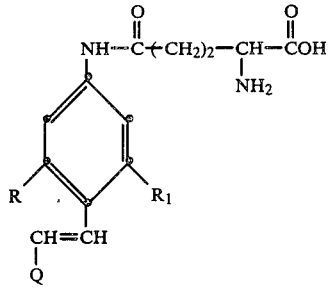

wherein:

R and R₁ are independently selected from hydrogen, alkyl and alkoxy and

Q is

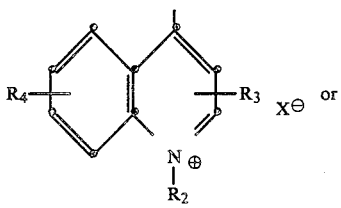 or

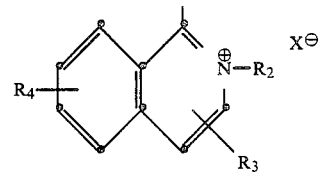

wherein:

R₂ is alkyl having from 1 to 4 carbon atoms;

R₃, and R₄ are independently selected from hydrogen, alkyl, alkoxy, nitro, cyano and halogen;

X⊖ is an anion; and an acceptor for γ-glutamyl.

8. The element according to claim 7 wherein said acceptor is glycylglycine.

9. The element according to claim 7 wherein:

Q is

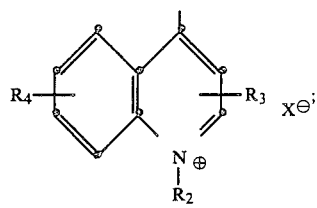

R, R₁, R₃ and R₄ are hydrogen;
R₂ is methyl; and
X⊖ is tetrafluoroborate.

10. A method for the determination of γ-glutamyl-transferase comprising the steps of (1) contacting a sample suspected of containing γ-glutamyltransferase with a reagent composition comprising a γ-glutamyl acceptor and a γ-glutamyltransferase substrate having the formula:

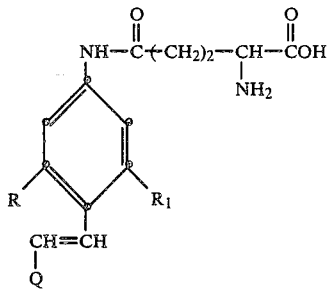

wherein:

R and R₁ are independently selected from hydrogen, alkyl and alkoxy and

Q is

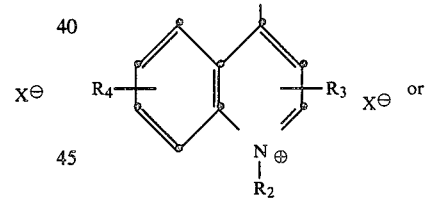 or

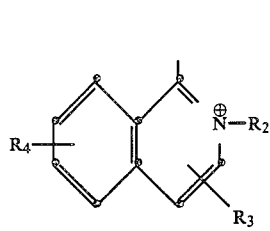

wherein:

R₂ is alkyl having from 1 to 4 carbon atoms;
R₃ and R₄ are independently selected from hydrogen, alkyl, alkoxy, nitro, cyano and halogen;
X⊖ is an anion;

(2) measuring the rate at which the aminostyryl-quinolinium dye is produced; and (3) relating said measured rate to the concentration of γ-glutamyltransferase in said sample.

* * * * *